United States Patent [19]

Elias et al.

[11] Patent Number: 5,181,427
[45] Date of Patent: Jan. 26, 1993

[54] THERMALLY-RELEASABLE-SAMPLE COLLECTING DEVICE

[75] Inventors: Lorne Elias, Nepean; André H. Lawrence, Gloucester; Francis W. Lemon, Ottawa, all of Canada

[73] Assignee: National Research Council of Canada, Ottawa, Canada

[21] Appl. No.: 689,483

[22] Filed: Apr. 23, 1991

[30] Foreign Application Priority Data

May 2, 1990 [CA] Canada ................................ 2015971

[51] Int. Cl.⁵ .............................................. G01N 1/24
[52] U.S. Cl. .............................. 73/863.12; 73/864.34
[58] Field of Search ............ 73/863.12, 863.21, 863.34

[56] References Cited

U.S. PATENT DOCUMENTS

| | | | |
|---|---|---|---|
| 3,645,694 | 2/1972 | Flatau | 73/863.21 X |
| 4,170,901 | 10/1979 | Conkle et al. | 73/863.12 |
| 4,350,037 | 9/1982 | Highan | 73/863.21 |
| 4,470,315 | 9/1984 | Ellgehauser et al. | 73/863.21 X |
| 4,584,887 | 4/1986 | Golan | 73/863.21 X |
| 4,890,502 | 1/1990 | Elias et al. | 73/864.85 |

Primary Examiner—Tom Noland
Attorney, Agent, or Firm—Francis W. Lemon

[57] ABSTRACT

A thermally-releasable-sample collecting device is provided comprising a pistol-shaped casing, a blunt ended probe in the front end of the casing barrel, an adsorber tube locating collar in a rear end of the casing barrel, and an adsorber tube slidably located in the collar and having an open ended, sample adsorber end portion in a central portion of a gas passage extending through the probe. The adsorber tube has a closed rear end and gas ports which are located by a spring loaded plunger in a first position for drawing air through the probe into the adsorber tube, and a second position where carrier gas passes along the adsorber tube, to entrain thermally released sample, while the sample adsorber end portion is protruding from the probe into the heated entry of an analyzer.

7 Claims, 1 Drawing Sheet

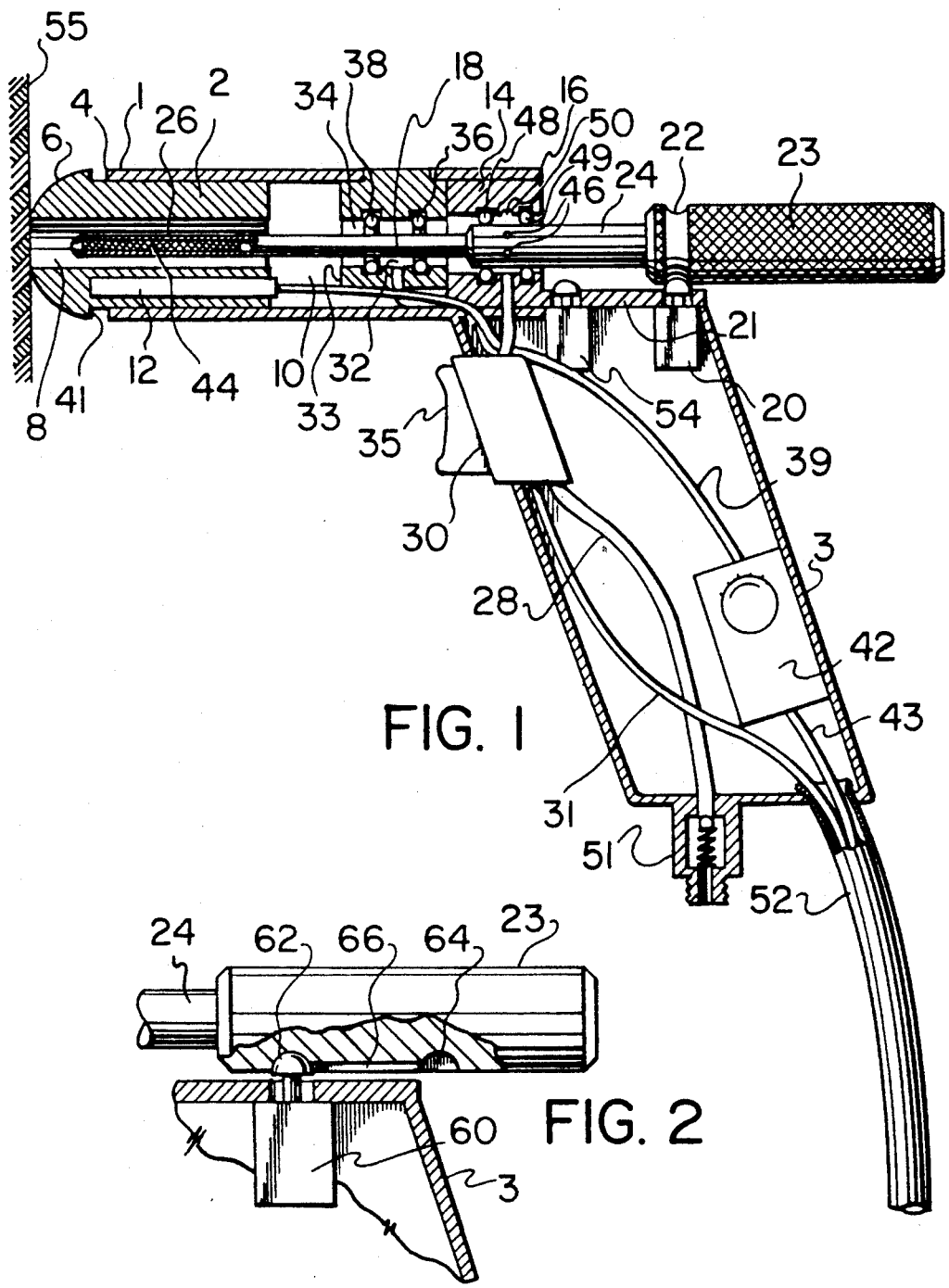

THERMALLY-RELEASABLE-SAMPLE COLLECTING DEVICE

FIELD OF THE INVENTION

This invention relates to a thermally-releasable-sample collecting device.

DESCRIPTION OF THE RELATED ART

It has already been proposed in "Analysis of Explosives and Explosive Residues With Ion Mobility Spectrometry (IMS)", G. E. Spangler, J. P. Carrico and S. H. Kim, Proceedings of the International Symposium on the Analysis and Detection of Explosives, FBI Academy, Quantico, Va., U.S.A., Mar. 29-31, 1983, to provide a surface sampler comprising a tungsten halogen lamp for heating a surface, and a sampler cone which is placed over the surface and within which swirling air jets entrain a vapour sample, thermally released from the surface, and swirl it up to transport lines to the IMS.

While the sampler of Spangler et al is useful, the long transport lines cause unacceptable losses when the vapour sample is a trace sample, and the tungsten halogen lamp cannot be relied on for thermally releasing a trace vapour sample for collection as the cone is moved across a surface.

There is a need for a thermally-releasable-sample collecting device which is capable of adsorbing a trace sample for, for example, IMS analysis, and which is capable of thermally releasing the adsorbed trace sample for entrainment by a purging gas into a heated entry port of an analyzer.

SUMMARY OF THE INVENTION

According to the present invention there is provided a sample collecting device, comprising:

a) a pistol-shaped casing, having an open ended, tubular barrel portion and a handle portion, b) a surface probe, secured and sealed to a front end of the tubular, barrel portion, the probe having an exposed, blunt, front end and a sample passage extending therethrough from the blunt end to the tubular, barrel portion interior, c) an adsorber tube locating collar secured and sealed to a rear end of the tubular, barrel portion, d) an adsorber tube having a front, open, sample adsorbent end portion, e) means releasably securing the adsorber tube within the tubular, barrel portion with a rear end portion of the adsorber tube located in the collar and the front, open, sample adsorbent end portion of the adsorber tube located in a central portion of the sample passage of the probe and terminating therein adjacent the blunt end of the probe, and f) means for drawing air into and along the adsorber tube from the front, open, sample adsorbent end portion thereof.

Preferably the surface probe is of heat conducting material, and heating means are provided for heating the probe for, in operation, thermally releasing a sample from a surface contacted by the probe.

The heating device may be an electrical heating cartridge in the probe, and a heat control may be provided which is electrically connected to, and controls the heating of the heating cartridge.

The means for releasably securing the adsorber tube within the tubular, barrel portion may comprise a spring loaded plunger assembly in the casing, the spring plunger assembly having a spring loaded plunger which engages in a first spring loaded plunger engaging recess in the adsorber tube when the front, open, sample adsorbent end portion of the adsorbent tube is located in the sample passage of the probe and terminates therein.

Means may be provided for locating the probe in a heated entry of a sample analyzer, and a second spring loaded plunger engaging recess may be provided in the adsorber tube which is engaged by the spring loaded plunger when the adsorbent end portion of the adsorber tube protrudes from the probe.

The rear end portion of the adsorber tube may be closed, at least one gas entry port may be provided in the adsorber tube rearwardly of the front, open, sample adsorbent end portion, and means may be provided for connecting the said at least one gas entry port to the means for drawing air into and along the adsorber tube when the spring loaded plunger is in engagement with the first recess, and for feeding a sample carrier gas entry port when the spring loaded plunger is in engagement with the second recess.

A trigger valve may be provided in the handle portion for controlling the feed of carrier gas to the adsorber tube.

BRIEF DESCRIPTION OF THE DRAWING

In the accompanying drawings which illustrate, by way of example, embodiments of the present invention, FIG. 1 is a partly sectioned side view of a thermally-releasable-sample collecting device, and FIG. 2 a partly sectioned side view of a different spring loaded plunger, adsorber tube locating arrangement to that shown in FIG. 1.

DESCRIPTION OF THE PREFERRED EMBODIMENT

In FIG. 1 there is shown a thermally-releasable-sample collecting device, comprising:

a) a pistol-shaped casing having an open ended, tubular, barrel portion 1 and a handle portion 3, b) a surface probe 2 secured and sealed to a front end 4 of the tubular, barrel portion 1, the probe 2 having an exposed, blunt, front end 6 and a sample passage 8 extending therethrough from the blunt end 6 to the tubular, barrel portion interior 10, c) an adsorber tube locating collar 14 secured and sealed to a rear end 16 of the tubular barrel portion 1, d) an adsorber tube 18 having a front, open, sample adsorbent end portion 26, e) means, in the form of a spring loaded plunger assembly 20, in an extension 21 of the collar 14, and a groove 22 in an adsorber tube handle 23, releasably securing the adsorber tube 18 within the tubular, barrel portion 1 with a rear end portion 24 of the adsorber tube 18 located in the collar 14 and the front, open, sample adsorbent end portion 26 of the adsorber tube 18 located in a central portion of the sample passage 8 of the probe 2 and terminating adjacent the blunt end 6, and f) means, in the form of an exhaust tube 28, for drawing air into and along the adsorber tube 18 from the front, sample adsorbent end portion 26 of the adsorber tube 18.

The handle 3 has a two position, solenoid valve switch 30 for interrupting the flow along the exhaust tube 28 and a purging gas inlet tube 31 leading to an annular passage 32 in a bore 34 in a second locating collar 33. In a forward position a trigger 35 of the valve switch 30 interrupts flow along both of the tubes 28 and 31. With the trigger 35 in a first activated position the valve switch 30 allows flow only along the purging gas inlet tube 31, and with the trigger switch retracted further to a second retracted position the valve switch allows flow only along the exhaust tube 28. The second locating collar 33 has two 0-ring seals 36 and 38.

The probe 2 is of stainless steel and forms an annular recess 41 with the tubular casing 1, which is a means for locating the device in the heated entry of an IMS (not shown).

A heating cartridge 12 is electrically connected by a cable 39 to a heat control 42 in the handle portion 3. The heat control 42 is connected to an electrical supply cable 43.

The adsorber tube 18 has an adsorber packing 44 in the front, open, sample adsorbent end portion 26. The rear end portion 24 of the adsorber tube 18 is larger than the front, open end portion 26 and has ports 46 spaced therearound leading to the bore thereof.

The adsorber tube locating collar 14 has O-ring seals 48 and 49 and an annular exhaust passage 50 connected to the exhaust tube 28. The exhaust tube 28 has a check valve 51.

The purging gas inlet tube 31 and the electrical cable 43 exit through the handle through a conduit 52. A further spring loaded plunger assembly 54 is provided in the extension 21 of the collar 14.

In operation, with the apparatus assembled as shown in FIG. 1 but with the adsorber tube 18 either removed or advanced to a forward position to protrude from the probe 2, the electrical cable 43 is connected to a power supply (not shown) and the exhaust check valve 51 is connected to a vacuum pump (not shown). Actuation of the heat control 42 will cause the heating cartridge to heat the probe 2. The trigger 35 is retracted to the second position so that the exhaust tube 28 will draw air into the adsorber tube 18 through the unheated adsorber packing 44 and assist in keeping the unheated adsorber packing 44 cool in combination with the space therearound provided by the passage 8.

When the probe 2 is heated sufficiently, the adsorber tube 18 is either inserted to, or retracted to, the position shown in FIG. 1. If the heated probe is now drawn along the surface of an article 55, thermally releasable substances of the article 55, or on the surface thereof, will be vaporized by the heated probe 2 and drawn with air into the adsorber tube 18 and trapped by the adsorbent packing 44. The trapping may be caused by condensation of the sample. The trigger 35 is then released to the forward position.

The front end of the casing 1 is then directly interfaced by means of the annular recess 41 with the heated entry of an IMS or other analyzer (not shown) and the handle 23 is pushed forward so that the groove 22 is located by the spring loaded plunger 54.

Movement of the groove 22 to the spring loaded plunger 54 causes the ports 46 to be aligned with the annular passage 32, and sealed on either side by the O-rings 36 and 38. A feed of purging gas, from a source, not shown, is now provided by moving the trigger 35 to the first retracted position and allow flow along the adsorber tube 18, so that purging gas flows over the adsorbent packing 44, and exits from the adsorber tube 18 into the IMS.

Movement of the groove 22 to the spring loaded plunger assembly 54 also causes the front, sample adsorbent end portion 26 of the adsorber tube 18 to protrude from the exposed, blunt, front end 6 into the heated entry port of the analyzer so that the substances trapped on the adsorbent packing 44 will be thermally released therefrom by heat from the heated entry of the analyzer. These thermally released chemicals are entrained in the purging gas entering the analyzer for subsequent analysis.

In other embodiments of the present invention, the non-return valve 30, the purging gas inlet tube 31, the O-rings 36 and 38, and the spring loaded plunger 54 are not provided, and the transfer of the chemicals from the adsorbent packing 44 to the IMS is carried out using the apparatus described and claimed in U.S. Pat. No. 4,890,502, dated Jan. 2, 1990, "A Sorbent Tube Trace Sample Releasing Apparatus", L. Elias and A. H. Lawrence.

In FIG. 2, similar parts to those shown in FIG. 1 are designated by the same reference numerals and the previous description is relied upon to describe them.

In FIG. 2, only one spring loaded plunger assembly 60 is provided and two recesses 62 and 64 are provided in the handle 23 with a semi-circular groove 66 extending between them.

In this embodiment, the spring loaded plunger assembly 60 engages the recess 62 while the adsorber tube 18 is adsorbing a sample, and the recess 62 when an adsorbed sample is being passed to an analyzer.

We claim:

1. A thermally-releasable-sample collecting device, comprising:
    a) a pistol-shaped casing, having an open ended, tubular barrel portion and a handle portion,
    b) a surface probe, secured and sealed to a front end of the tubular, barrel portion, the probe having an exposed, blunt, front end and a sample passage extending therethrough from the blunt end to the tubular, barrel portion interior,
    c) an adsorber tube locating collar secured and sealed to a rear end of the tubular, barrel portion,
    d) an adsorber tube having a front, open, sample adsorbent end portion,
    e) means releasably securing the adsorber tube within the tubular, barrel portion with a rear end portion of the adsorber tube located in the collar and the front, open, sample adsorbent end portion of the adsorbent tube located in a central portion of the sample passage of the probe and terminating therein adjacent the blunt end of the probe, and
    f) means for drawing air into and along the adsorbent tube from the front, open, sample adsorbent end portion thereof.

2. A device according to claim 1, wherein the surface probe is of heat conducting material, and heating means are provided for heating the probe for, in operation, thermally releasing a sample from a surface contacted by the probe.

3. A device according to claim 2, wherein the heating device is an electrical heating cartridge in the probe, and a heat control is provided which is electrically connected to, and controls the heating of the heating cartridge.

4. A device according to claim 1, wherein the means for releasably securing the adsorber tube within the tubular, barrel portion comprises a spring loaded plunger assembly in the casing, the spring plunger assembly having a spring loaded plunger which engages in a spring loaded plunger engaging first recess in the adsorber tube when the front, open, sample adsorbent end portion of the adsorber tube is located in the sample passage of the probe and terminates therein.

5. A device according to claim 4, wherein means are provided for locating the probe in a heated entry of a sample analyzer, and a second spring loaded plunger engaging recess is provided in the adsorber tube which is engaged by the spring loaded plunger when the adsorbent end portion of the adsorber tube protrudes from the probe.

6. A device according to claim 5, wherein the rear end portion of the adsorber tube is closed, at least one gas entry port is provided in the adsorber tube rearwardly of the front, open, sample adsorbent end portion, and means are provided for connecting the said at least one gas entry port to the means for drawing air into and along the adsorber tube when the spring loaded plunger is in engagement with the first recess, and for feeding a sample carrier gas entry port when the spring loaded plunger is in engagement with the second recess.

7. A device according to claim 6, further comprising a trigger valve in the handle portion for controlling the feed of carrier gas to the adsorber tube.

* * * * *